(12) United States Patent
Peyman

(10) Patent No.: US 9,427,355 B1
(45) Date of Patent: Aug. 30, 2016

(54) CORNEAL TRANSPLANTATION WITH A CROSS-LINKED CORNEA

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 14/709,801

(22) Filed: May 12, 2015

Related U.S. Application Data

(60) Provisional application No. 61/991,785, filed on May 12, 2014, provisional application No. 62/065,714, filed on Oct. 19, 2014.

(51) Int. Cl.
| | | |
|---|---|---|
| *A61F 2/14* | (2006.01) | |
| *A61F 9/008* | (2006.01) | |
| *A61L 27/36* | (2006.01) | |

(52) U.S. Cl.
CPC .............. *A61F 9/0081* (2013.01); *A61F 2/142* (2013.01); *A61F 9/00814* (2013.01); *A61L 27/3687* (2013.01); *A61F 2009/00872* (2013.01); *A61L 2430/16* (2013.01); *A61L 2430/40* (2013.01)

(58) Field of Classification Search
CPC ...................... A61F 9/008; A61F 2009/00842; A61F 2009/00861; A61F 2009/00872; A61F 9/0081; A61F 9/00812; A61F 2009/0885; A61F 2009/00893; A61F 2/142; A61F 2/145; A61F 2/1451; A61F 2210/00; A61F 2240/00–2240/002; A61F 2250/0091; A61L 2430/16; A61L 2430/40; A61L 27/3604; A61L 27/3641; A61L 27/3683; A61L 27/50
See application file for complete search history.

(56) References Cited

U.S. PATENT DOCUMENTS

| | | | |
|---|---|---|---|
| 3,760,807 A | | 9/1973 | Neefe |
| 4,563,779 A | * | 1/1986 | Kelman .................. A61F 2/142 128/898 |
| 4,665,913 A | | 5/1987 | L'Esperance, Jr. |
| 4,718,418 A | | 1/1988 | L'Esperance, Jr. |
| 4,793,344 A | * | 12/1988 | Cumming .................. A61F 2/14 606/1 |

(Continued)

FOREIGN PATENT DOCUMENTS

WO          01/58495 A2      8/2001

OTHER PUBLICATIONS

Goins et al, "Photodynamic biologic tissue glue to enhance corneal wound healing after radial keratotomy", (Nov. 1997), Journal of Cataract and Refractive Surgery, vol. 23, Issue 9, pp. 1331-1338. (Abstract only).*

(Continued)

*Primary Examiner* — Paul Prebilic
(74) *Attorney, Agent, or Firm* — The Law Office of Patrick F. O'Reilly III, LLC

(57) ABSTRACT

A method of corneal transplantation with a cross-linked cornea is disclosed herein. In one or more embodiments, the method includes the steps of: (i) cross-linking a portion of a donor cornea so as to kill donor keratocytes in the donor cornea and make the cross-linked donor cornea less antigenic to an eye of a recipient patient; (ii) removing a scarred and/or diseased cornea or corneal portion from the eye of the recipient patient; and (iii) implanting the cross-linked donor cornea into the eye of the recipient patient in a location previously occupied by the scarred and/or diseased cornea or corneal portion, wherein the cross-linking of the donor cornea eliminates an immune response of the recipient patient to the transplanted donor cornea. Both penetrating keratoplasty transplant procedures and lamellar keratoplasty transplant procedures using a cross-linked donor cornea are disclosed herein.

22 Claims, 7 Drawing Sheets

(56) References Cited

U.S. PATENT DOCUMENTS

| | | | |
|---|---|---|---|
| 4,799,931 A | 1/1989 | Lindstrom | |
| 4,840,175 A | 6/1989 | Peyman | |
| 4,903,695 A | 2/1990 | Warner et al. | |
| 4,994,058 A | 2/1991 | Raven et al. | |
| 5,171,318 A | 12/1992 | Gibson et al. | |
| 5,336,261 A | 8/1994 | Barrett et al. | |
| 5,552,452 A * | 9/1996 | Khadem | A61L 24/106 |
| | | | 522/2 |
| 5,964,748 A | 10/1999 | Peyman | |
| 6,110,166 A | 8/2000 | Juhasz | |
| 6,197,019 B1 | 3/2001 | Peyman | |
| 6,537,545 B1 | 3/2003 | Karageozian et al. | |
| 6,551,307 B2 | 4/2003 | Peyman | |
| 7,001,374 B2 | 2/2006 | Peyman | |
| 7,004,902 B2 | 2/2006 | Luce | |
| 7,044,945 B2 | 5/2006 | Sand | |
| 9,301,925 B2 * | 4/2016 | Xu | A61L 27/38 |
| 2001/0027314 A1 * | 10/2001 | Peyman | A61F 2/14 |
| | | | 606/5 |
| 2002/0006394 A1 * | 1/2002 | Redmond | A61F 9/0079 |
| | | | 424/93.7 |
| 2003/0035843 A1 * | 2/2003 | Livesey | A01N 1/00 |
| | | | 424/549 |
| 2004/0029855 A1 * | 2/2004 | Klaveness | A61K 9/006 |
| | | | 514/185 |
| 2007/0135754 A1 | 6/2007 | Akiyama et al. | |
| 2007/0142908 A1 * | 6/2007 | Xu | A01N 1/00 |
| | | | 623/5.16 |
| 2009/0171305 A1 | 7/2009 | El Hage | |
| 2010/0198348 A1 * | 8/2010 | Hiles | A61F 2/142 |
| | | | 623/5.16 |
| 2010/0210996 A1 * | 8/2010 | Peyman | A61F 7/007 |
| | | | 604/20 |
| 2010/0215717 A1 * | 8/2010 | Soker | A61F 2/142 |
| | | | 424/423 |
| 2011/0076734 A1 * | 3/2011 | Zhou | C12N 5/0062 |
| | | | 435/173.1 |
| 2011/0152219 A1 * | 6/2011 | Stagni | A61K 9/0048 |
| | | | 514/81 |
| 2011/0250688 A1 * | 10/2011 | Hasan | C12N 5/0062 |
| | | | 435/395 |
| 2012/0203161 A1 * | 8/2012 | Herekar | A61K 9/0048 |
| | | | 604/20 |

OTHER PUBLICATIONS

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).*

Wollensak et al., "Riboflavin/Ultraviolet-A—induced Collagen Crosslinking for the Treatment of Keratoconus", American Journal of Ophthalmology, vol. 135, pp. 620-627 (2003), (May 2003).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.

* cited by examiner

CORNEAL TRANSPLANTATION WITH A CROSS-LINKED CORNEA

CROSS-REFERENCE TO RELATED APPLICATIONS

This patent application claims priority to U.S. Provisional Patent Application No. 61/991,785, entitled "Corneal Transplantation With A Cross-Linked Cornea", filed on May 12, 2014; and further claims priority to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to corneal transplantation. More particularly, the invention relates to methods for corneal transplantation with a cross-linked cornea.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, and other corneal dystrophies. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells.

BRIEF SUMMARY OF EMBODIMENTS OF THE INVENTION

Accordingly, the present invention is directed to one or more methods of corneal transplantation with cross-linked corneas that substantially obviate one or more problems resulting from the limitations and deficiencies of the related art.

In accordance with one or more embodiments of the present invention, there is provided a method of corneal transplantation with a cross-linked cornea, the method comprising the steps of: (i) cross-linking a portion of a donor cornea so as to kill donor keratocytes in the donor cornea and make the cross-linked donor cornea less antigenic to an eye of a recipient patient; (ii) removing a scarred and/or diseased cornea from the eye of the recipient patient; and (iii) implanting the cross-linked donor cornea into the eye of the recipient patient in a location previously occupied by the scarred and/or diseased cornea, wherein the cross-linking of the donor cornea eliminates an immune response of the recipient patient to the transplanted donor cornea. The cross-linked cornea may be formed to the desired shape that is required for implantation.

In a further embodiment of the present invention, the step of cross-linking a portion of a donor cornea comprises cross-linking a front portion of the donor cornea. In another further embodiment, cross-linking may be performed on up to four-fifths (⅘) of the donor cornea as needed while the donor cornea is under observation by an optical coherence tomography (OCT) system. As such, this provides a controlled way of cross-linking the cornea. The OCT system can demonstrate increased density of the cornea after crosslinking.

In yet a further embodiment, the step of cross-linking a portion of a donor cornea comprises the steps of: (iv) applying a photosensitizer to the portion of the donor cornea, the photosensitizer facilitating cross-linking of the donor cornea; and (v) irradiating the portion of the donor cornea with ultraviolet light so as to activate cross-linkers in the portion of the donor cornea and thereby strengthen the portion of the donor cornea.

In still a further embodiment, the photosensitizer comprises riboflavin, and the portion of the donor cornea is irradiated by using a laser.

In yet a further embodiment, the step of irradiating the portion of the donor cornea with ultraviolet light comprises irradiating the portion of the donor cornea with ultraviolet light having a wavelength between about 370 nanometers and about 380 nanometers. In other further embodiments, other wavelengths of radiation may be used along with a photosensitizer.

In still a further embodiment, the step of removing a scarred and/or diseased cornea from the eye of the recipient patient comprises removing substantially the entire thickness of the cornea from the eye of the recipient patient.

In yet a further embodiment, the step of removing a scarred and/or diseased cornea from the eye of the patient comprises initially cutting away or dissecting a scarred and/or diseased portion of the cornea from a remainder of the cornea using a sharp mechanical instrument, a femtosecond laser, or a combination of a sharp mechanical instrument and a femtosecond laser, and then subsequently removing the scarred and/or diseased portion of the cornea from the eye using a pair of micro-forceps.

In still a further embodiment, the sharp mechanical instrument comprises one of: (i) a surgical micro-knife, (ii) a needle, (iii) a sharp spatula, and (iv) a pair of micro-scissors.

In accordance with one or more other embodiments of the present invention, there is provided a method of corneal transplantation with a cross-linked cornea, the method comprising the steps of: (i) removing a scarred and/or diseased portion of a cornea from an eye of a patient; (ii) implanting a portion of a donor cornea into the eye of the patient in a location previously occupied by the scarred and/or diseased portion of the cornea; and (iii) cross-linking the portion of the donor cornea either prior to the step of implanting the portion of the donor cornea into the eye of the patient or after the step of implanting the portion of the donor cornea into the eye of the patient so as to increase a mechanical strength of the donor cornea.

In a further embodiment of the present invention, the step of removing a scarred and/or diseased portion of a cornea from an eye of a patient comprises removing an external portion of the cornea from outside the eye of the patient.

In yet a further embodiment, the step of removing a scarred and/or diseased portion of a cornea from an eye of a patient comprises removing the scarred and/or diseased portion of the cornea from the eye of the patient by cutting away the scarred and/or diseased portion of the cornea using a laser.

In still a further embodiment, the laser comprises a femtosecond laser.

In yet a further embodiment, the step of removing a scarred and/or diseased portion of a cornea from an eye of a patient comprises removing an internal portion of the cornea from the eye of the patient.

In still a further embodiment, the internal portion of the cornea is removed using forceps.

In yet a further embodiment, the method further comprises the step of, after implantation and cross-linking of the portion of the donor cornea, ablating a portion of the cornea of the patient so as to change the refractive properties of the eye.

In still a further embodiment, the portion of the cornea of the patient is ablated using an excimer laser after the transplantation of the donor cornea.

In yet a further embodiment, the method further comprises the step of, prior to implantation of the portion of the donor cornea, ablating an external surface or an internal surface of the portion of the donor cornea so as to change the refractive properties of the portion of the donor cornea.

In still a further embodiment, the external surface or the internal surface of the portion of the donor cornea is ablated using an excimer laser.

In yet a further embodiment, the method further comprises the step of, prior to implantation of the portion of the donor cornea, ablating an external surface or an internal surface of the cornea of the eye of the patient.

In still a further embodiment, the external surface or the internal surface of the cornea of the eye of the patient is ablated using an excimer laser.

In yet a further embodiment, the method further comprises the step of securing the portion of the donor cornea to the cornea of the eye of the patient using either a suture or an adhesive.

In still a further embodiment, the step of securing the portion of the donor cornea to the cornea of the eye of the patient comprising securing the portion of the donor cornea using an adhesive, the adhesive comprising a biocompatible and biodegradable adhesive that does not require exothermic energy for adhesion to the eye of the patient, the biocompatible and biodegradable adhesive including combinations of gallic acid, gallic tannic acid, Chitosan, gelatin, polyphenyl compound, Tannic Acid (N-isopropylacrylamide (PNI-PAM), and/or Poly(N-vinylpyrrolidone) with polyethylene glycol (PEG).

In accordance with yet one or more other embodiments of the present invention, there is provided a method of corneal transplantation with a cross-linked cornea, the method comprising the steps of: (i) applying a photosensitizer to a portion of a donor cornea, the photosensitizer facilitating cross-linking of the donor cornea; (ii) irradiating the portion of the donor cornea with ultraviolet light, visible light, or infrared light so as to activate cross-linkers in the portion of the donor cornea and thereby stiffen the portion of the donor cornea; (iii) removing at least a scarred and/or diseased portion of a cornea from an eye of a patient; and implanting the cross-linked donor cornea into the eye of the patient in a location previously occupied by the scarred and/or diseased portion of the cornea.

In a further embodiment of the present invention, the photosensitizer comprises riboflavin or another suitable photosensitizer.

In yet a further embodiment, the portion of the donor cornea is irradiated by using a laser.

In still a further embodiment, the step of irradiating the portion of the donor cornea with ultraviolet light comprises irradiating the portion of the donor cornea with ultraviolet light having a wavelength between about 370 nanometers and about 380 nanometers.

In yet a further embodiment, the method further comprises the step of, after implantation of the cross-linked donor cornea into the eye of the patient, ablating a portion of the cornea of the patient so as to change the refractive properties of the eye.

In still a further embodiment, the step of removing at least a scarred and/or diseased portion of a cornea from an eye of a patient comprises removing the scarred and/or diseased portion of the cornea from the eye of the patient by cutting away the scarred and/or diseased portion of the cornea using a laser.

In yet a further embodiment, the laser comprises a femtosecond laser.

In still a further embodiment, the step of removing at least a scarred and/or diseased portion of a cornea from an eye of a patient comprises initially cutting away or dissecting the scarred and/or diseased portion of the cornea from a remainder of the cornea using a sharp mechanical instrument, and then subsequently removing the scarred and/or diseased portion of the cornea from the eye using a pair of micro-forceps.

In yet a further embodiment, the sharp mechanical instrument comprises one of: (i) a surgical micro-knife, (ii) a needle, (iii) a sharp spatula, and (iv) a pair of micro-scissors.

In accordance with still one or more other embodiments of the present invention, there is provided a method of corneal transplantation with a cross-linked cornea, the method comprising the steps of: (i) removing a scarred and/or diseased portion of a cornea from an eye of a patient; (ii) implanting a portion of a donor cornea into the eye of the patient in a location previously occupied by the scarred and/or diseased portion of the cornea; and (iii) cross-linking the portion of the donor cornea after the step of implanting the portion of the donor cornea into the eye of the patient.

In a further embodiment of the present invention, the method further comprises the step of ablating an external surface or an internal surface of the cornea of the eye of the patient with an excimer laser prior to the step of implanting the portion of the donor cornea into the eye of the patient or after the step of implanting the portion of the donor cornea into the eye of the patient.

In accordance with yet one or more other embodiments of the present invention, there is provided a method of corneal transplantation with a cross-linked cornea, said method comprising the steps of: (i) forming a corneal pocket in an eye of a recipient patient; (ii) cross-linking at least a portion of a donor cornea so as to kill donor keratocytes in the portion of the donor cornea and make the portion of the donor cornea less antigenic to the eye of the recipient patient; (iii) forming a lamellar lenslet from the cross-linked portion of the donor cornea, and removing the cross-linked lamellar lenslet from a remainder of the donor cornea; and (iv) implanting the cross-linked lamellar lenslet into the corneal pocket in the eye of the recipient patient, whereby the implantation of the cross-linked lamellar lenslet into the eye of the recipient patient both corrects refractive errors of the eye of the recipient patient and eliminates an immune response of the recipient patient to the transplanted cross-linked lamellar lenslet.

In a further embodiment of the present invention, the step of forming a lamellar lenslet from the cross-linked portion of the donor cornea comprises shaping the cross-linked lamellar lenslet with a femtosecond laser or an excimer laser prior to implantation into the eye of the recipient patient in order to create a custom lens that corrects the refractive errors specific to the recipient patient.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
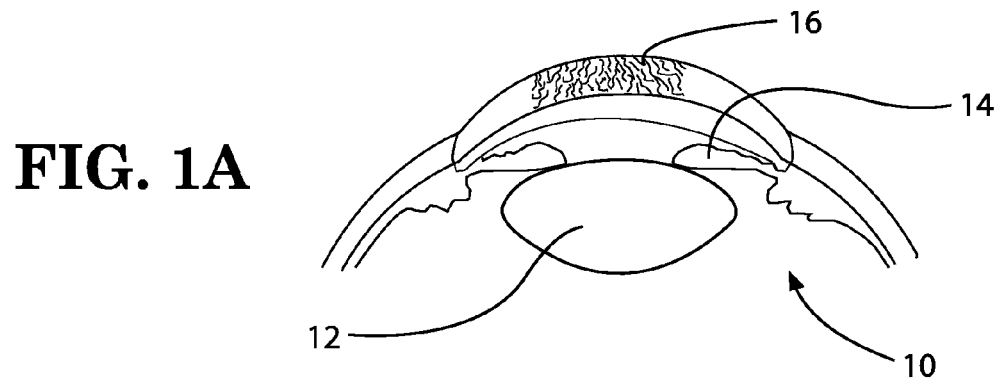
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
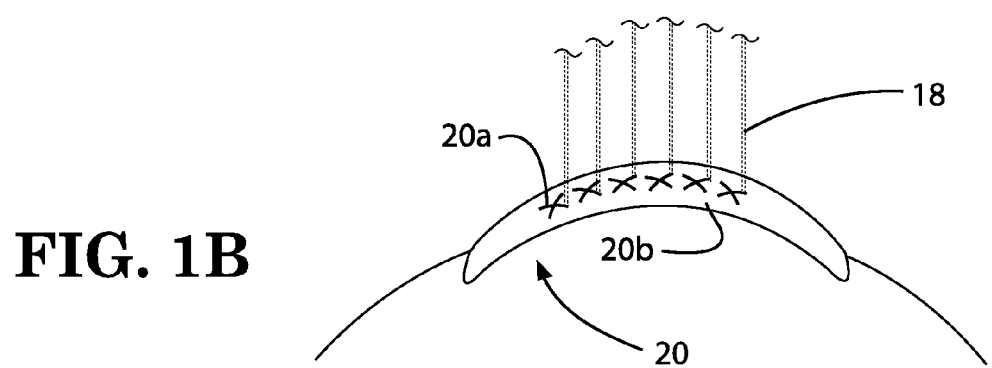
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the cross-linking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The cross-linker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
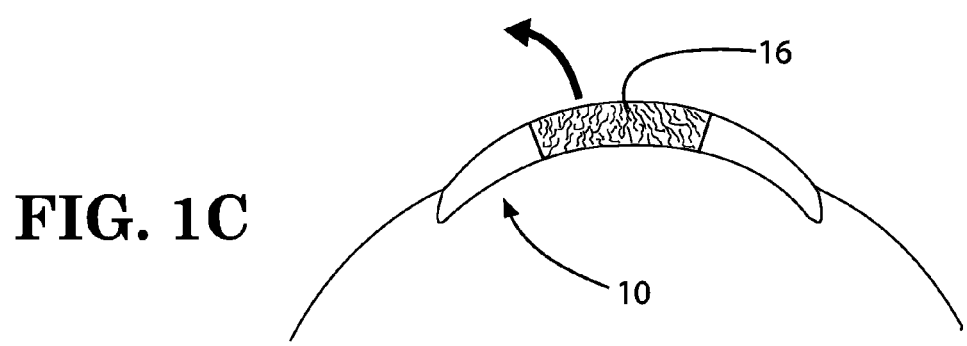
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
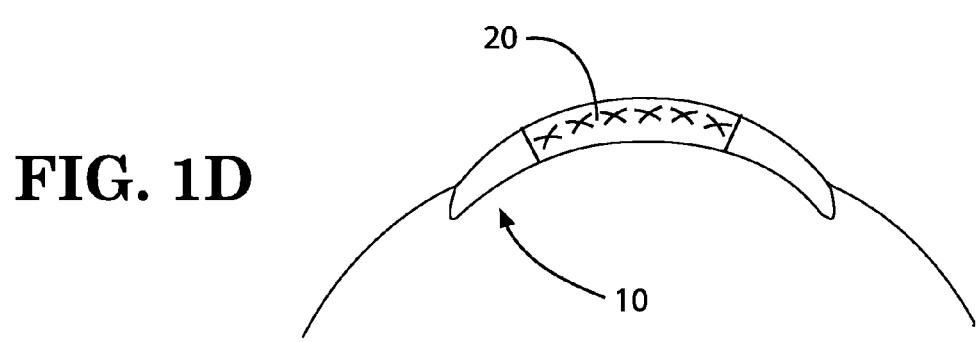
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a non-cross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

Figure 2A:
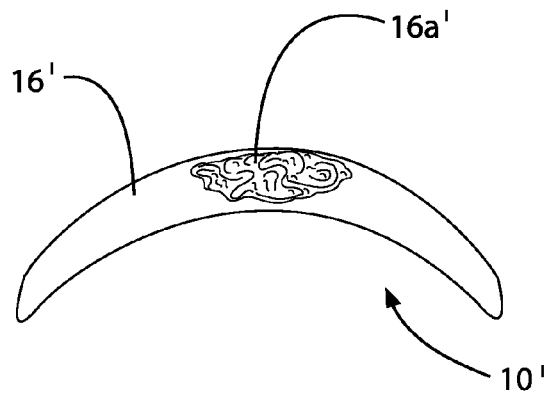
FIG. 2A is a partial side cross-sectional view of an eye having internal corneal scar tissue.
Figure 2B:
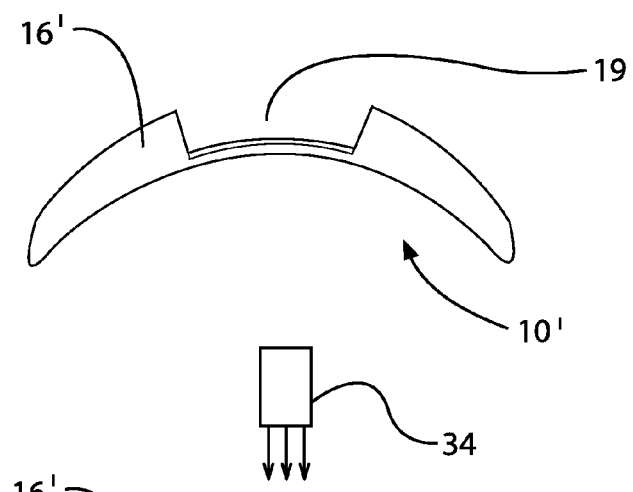
FIG. 2B is a partial side cross-sectional view of the eye of FIG. 2A, wherein the scarred corneal tissue has been externally removed from the eye.
Figure 2C:
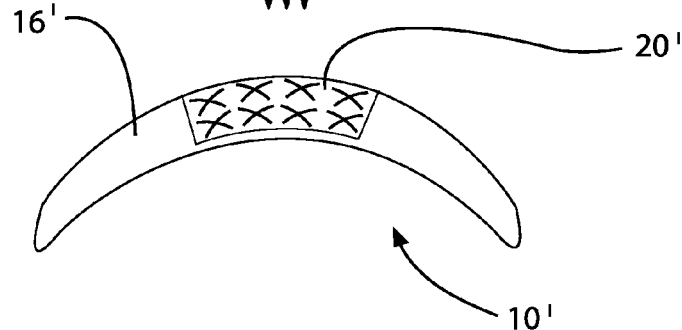
FIG. 2C is a partial side cross-sectional view of the eye of FIG. 2A, wherein a cross-linked donor cornea is shown being implanted in the location previously occupied by the scarred corneal tissue.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
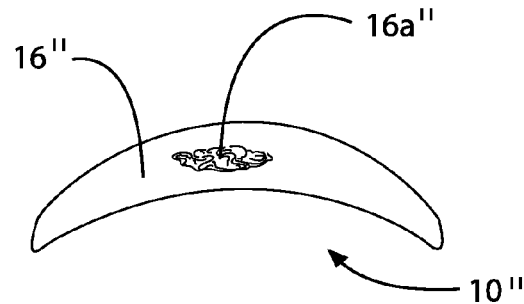
FIG. 3A is a partial side cross-sectional view of an eye having internal corneal scar tissue.
Figure 3B:
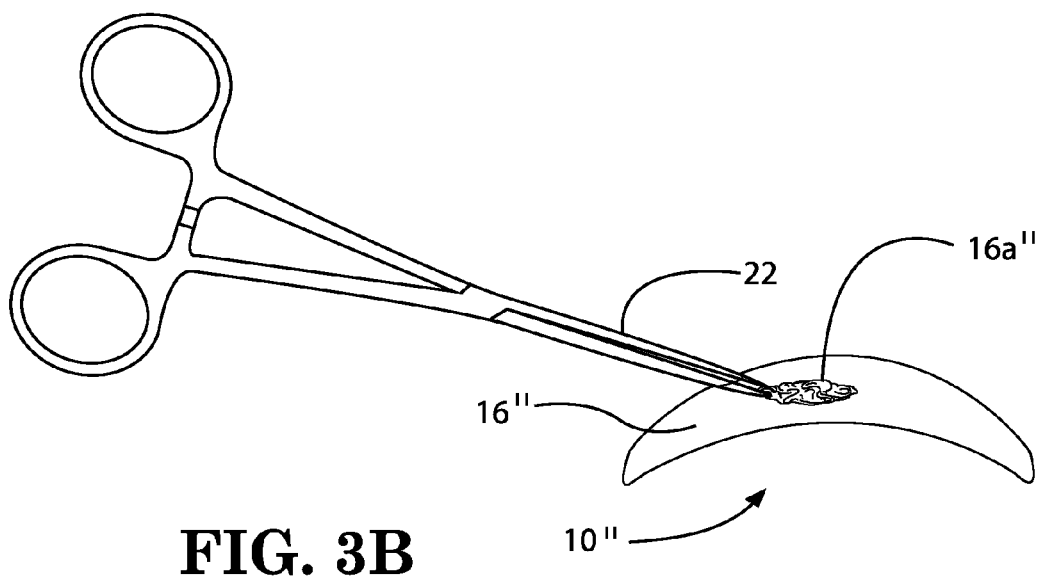
FIG. 3B is a partial side cross-sectional view of the eye of FIG. 3A, wherein the scarred corneal tissue is shown being internally removed from the eye.
Figure 3C:
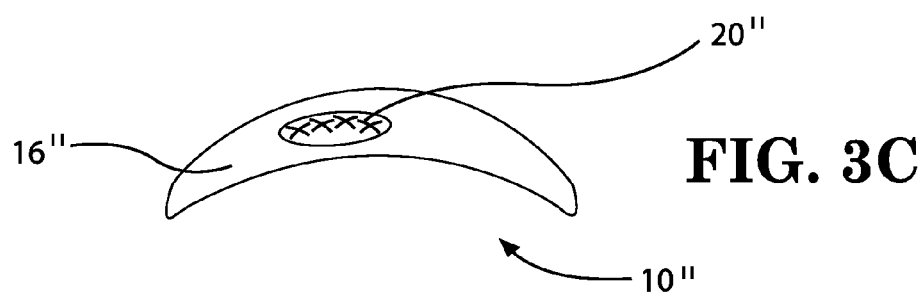
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a''' of the cornea 16''' with a donor corneal portion. Thus, similar to the second and third embodiments explained above, FIGS. 4A-4E illustrate a lamellar keratoplasty procedure wherein only a portion of the cornea 16''' of the eye 10''' contains scarred and/or diseased tissue (i.e., a full-thickness corneal section is not removed). Although, in the procedure of FIGS. 4A-4E, a different-shaped scarred and/or diseased portion 16a''' of the cornea 16''' is removed.

Figure 4A:
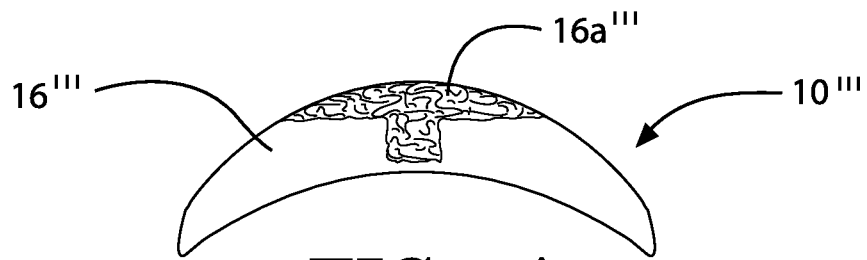
FIG. 4A is a partial side cross-sectional view of an eye having a T-shaped corneal scar and/or diseased tissue portion.

Referring initially to FIG. 4A, it can be seen that only a portion 16a''' of the cornea 16''' having a T-shape or "top hut" shape is scarred and/or diseased. As such, in this embodiment, it is not necessary to replace the entire thickness of the cornea 16''' with a donor cornea as was described above in conjunction with FIGS. 1A-1D, but rather just a portion 16a''' of the cornea 16'''. In this illustrative embodiment, the back side of the cornea 16''' is maintained (see e.g., FIG. 4D).

Figure 4B:
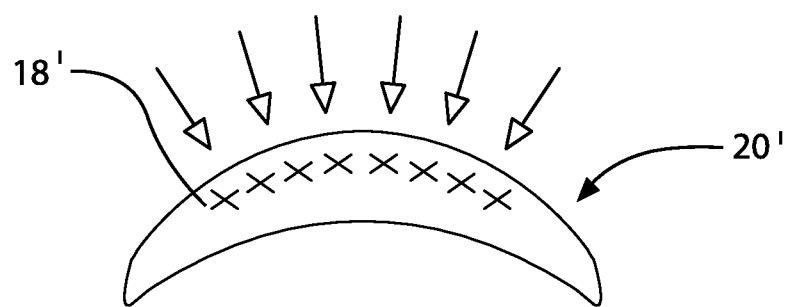
FIG. 4B is another partial side cross-sectional view of a donor cornea undergoing cross-linking.
Figure 4C:
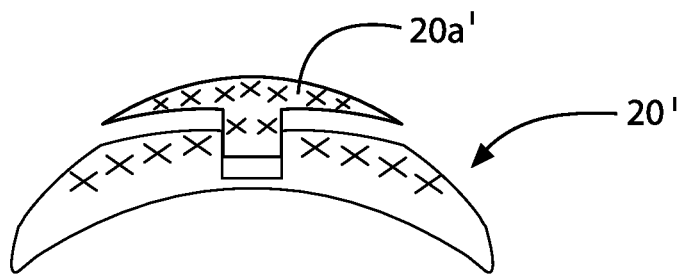
FIG. 4C is a partial side cross-sectional view illustrating a T-shaped portion of the cross-linked donor cornea being cut out from a remainder of the donor cornea.
Figure 5A:
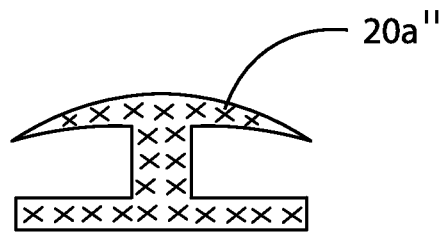
FIG. 5A illustrates an alternative configuration for the cross-linked donor cornea implant, wherein the donor cornea implant has a dumbbell shape.
Figure 5B:
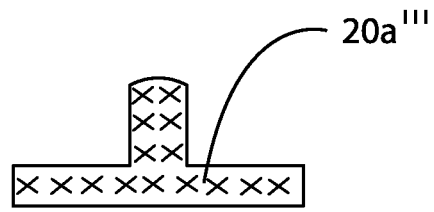
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a''' of the cornea 16''', is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a" (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
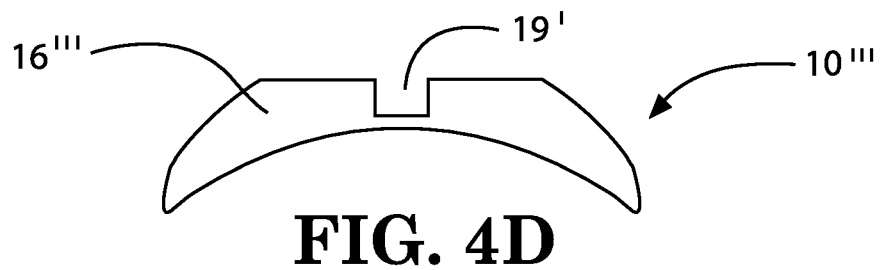
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16a''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16a''' may be removed from the remainder of the cornea 16''' using various suitable means, such as mechanical means or the laser cutting means (e.g., femtosecond laser) described above.

Figure 4E:
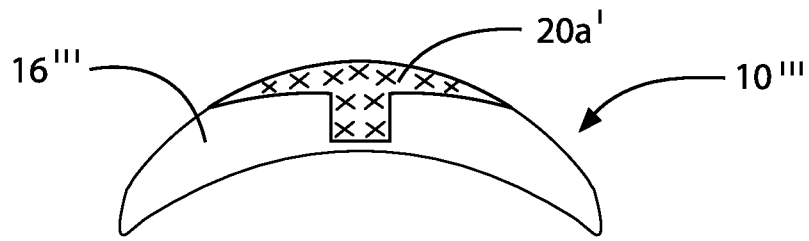
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16a''' has been removed from the remainder of the cornea 16''' of the eye 10''', the cross-linked donor corneal portion 20a' is implanted into the eye 10''' of the patient in the location previously occupied by the scarred and/or diseased corneal portion 16a'''. Because the shape of the transplant corresponds to that of the removed portion 16a''' of the cornea 16''', the transplant sits comfortably in its position in the host cornea. As described above, after implantation of the cross-linked donor corneal portion 20a' into the eye 10''', sutures or a suitable adhesive (e.g., the biocompatible and biodegradable adhesive described above) may be utilized to secure the cross-linked donor corneal portion 20a' in place on the host cornea 16''' of the eye 10'''. For example, if a biocompatible and biodegradable adhesive is used to secure the cross-linked donor corneal portion 20a' in place in the cornea 16''' of the eye 10''', the edges of the donor corneal portion 20a' are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

A fifth illustrative embodiment of a corneal transplant procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16'''' of the host eye 10'''' is removed during the procedure (i.e., a full-thickness corneal section is not removed). Although, the procedure of FIGS. 6A-6C and 7A-7C differs in several important respects from the abovedescribed procedures. In the fifth embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16'''' of the host eye 10''''. After making an internal pocket 28 in the recipient cornea 16'''' of the host eye 10'''' with a femtosecond laser, the cross-linked transplant is folded and implanted in a predetermined fashion inside the host's corneal pocket 28 to provide stability to the eye 10'''' having keratoconus, keratoglobus, a thin cornea or abnormal corneal curvature, thereby preventing future corneal ectasia in this eye 10'''' and correcting its refractive errors. Advantageously, the procedure of the fifth embodiment comprises a lamellar cross-linked corneal transplantation, which additionally results in simultaneous correction of the refractive error of the eye 10'''' of the patient.

Figure 6A:
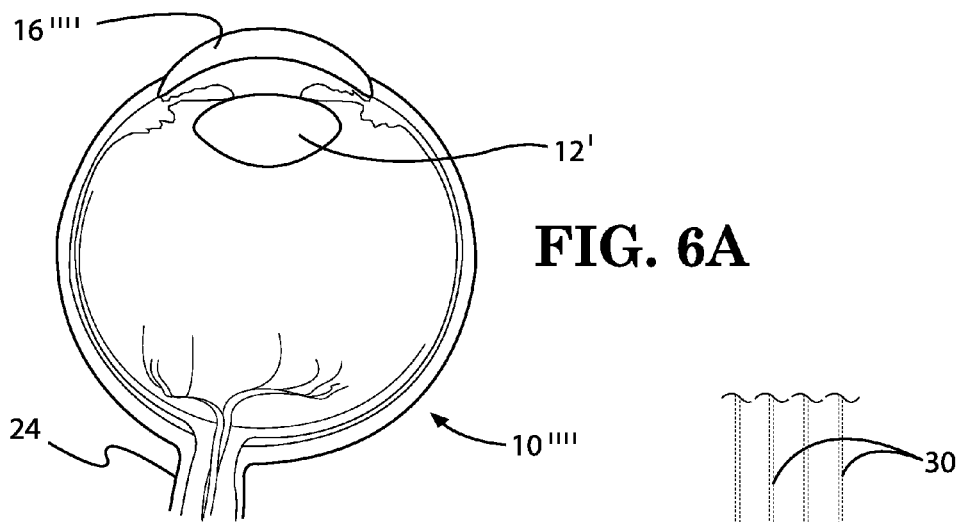
FIG. 6A is a side cross-sectional view of a host eye prior to an transplant procedure.
Figure 6B:
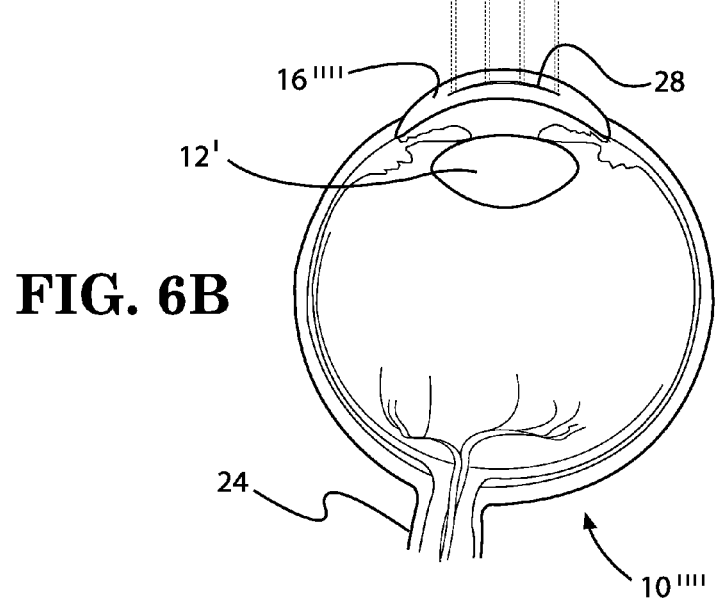
FIG. 6B is another side cross-sectional view of the host eye of FIG. 6A, which illustrates a creation of a corneal pocket therein.

Now, with reference to FIGS. 6A-6C and 7A-7C, the fifth illustrative embodiment will be described in further detail. The host eye 10'''' with lens 12', cornea 16'''', and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16'''' of the host eye 10'''' (e.g., by using a suitable laser, which is indicated diagrammatically in FIG. 6B by lines 30).

Figure 7A:
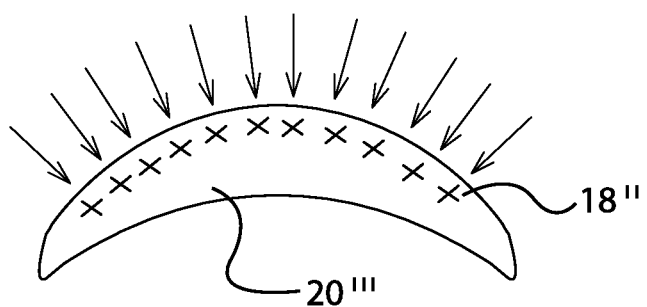
FIG. 7A is a partial side cross-sectional view of a donor cornea being cross-linked prior to being shaped for use in a transplant procedure.
Figure 7B:
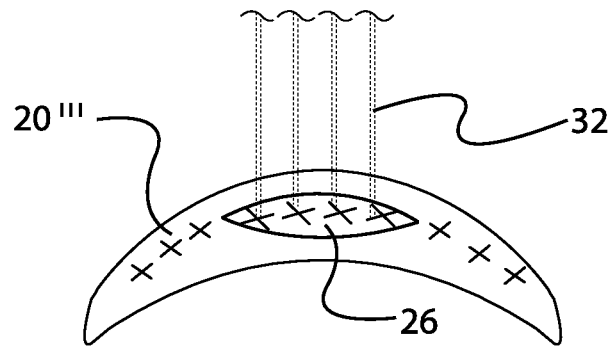
FIG. 7B is another partial side cross-sectional view of the donor cornea of FIG. 7A, which illustrates the cutting of a cross-linked lamellar lenslet from a remainder of the cross-lined donor cornea.
Figure 7C:
FIG. 7C is a side cross-sectional view of the cross-linked lamellar lenslet after it has been appropriately shaped and removed from the donor cornea of FIGS. 7A and 7B.

In FIG. 7A, the cross-linking 18'' of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked, it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10''''. As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20'''.

Figure 6C:
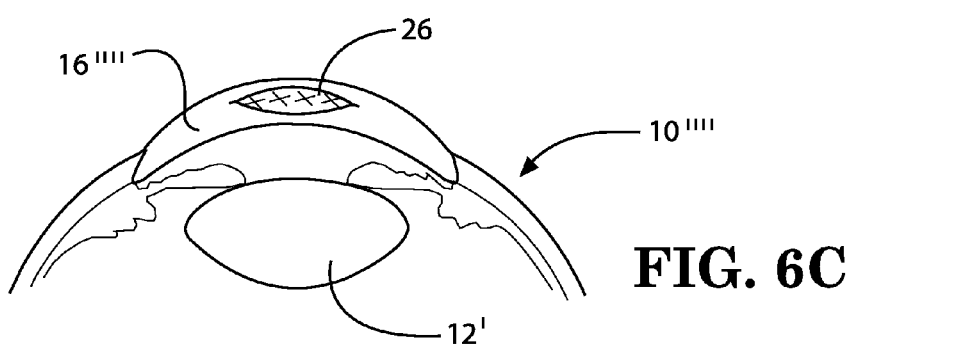
FIG. 6C is another side cross-sectional view of the host eye of FIG. 6A, which illustrates an implantation of the cross-linked lamellar lenslet into the host eye.

Finally, as shown in FIG. 6C, the cross-linked lamellar lenslet 26 is implanted into the cornea 16'''' of the host eye 10'''' of the patient in the location where the pocket 28 was previously formed. Because the shape of the transplant corresponds to that of the pocket 28 formed in the eye 10'''', the transplant sits comfortably in its position in the host cornea 16''''. As described above, after implantation of the cross-linked lamellar lenslet 26 into the eye 10'''', the refractive errors of the eye 10'''' have been corrected because the cross-linked lamellar lenslet 26 has been appropriately shaped to compensate for the specific refractive errors of the host eye 10'''' prior to its implantation into the eye 10''''. In addition, as explained above, the implantation of the cross-linked lamellar lenslet 26 provides additional stability to an eye having keratoconus, keratoglobus, a thin cornea, or abnormal corneal curvature.

It is readily apparent that the aforedescribed corneal transplant procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of abovedescribed tissue adhesives reduces the surgical procedure significantly.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of corneal transplantation with a cross-linked cornea, said method comprising the steps of:

applying a photosensitizer to a portion of a donor cornea, the photosensitizer facilitating cross-linking of the collagen of the donor cornea;

irradiating the portion of the donor cornea with ultraviolet light so as to activate cross-linkers in the portion of the donor cornea, and thereby cross-link the portion of the donor cornea so as to strengthen the portion of the donor cornea, kill donor keratocytes in the cross-linked donor cornea, and make the cross-linked donor cornea less antigenic to an eye of a recipient patient;

removing a scarred and/or diseased cornea from the eye of the recipient patient;

implanting the cross-linked donor cornea into the eye of the recipient patient in a location previously occupied by the scarred and/or diseased cornea, wherein the cross-linking of the donor cornea eliminates an immune response of the recipient patient to the transplanted donor cornea; and after cross-linking and implantation of the cross-linked donor cornea, securing the cross-linked donor cornea to the eye of the patient using a biocompatible and biodegradable adhesive.

2. The method according to claim 1, wherein the step of cross-linking the portion of a donor cornea comprises cross-linking a front portion of the donor cornea.

3. The method according to claim 1, wherein the photosensitizer comprises riboflavin, and wherein the portion of the donor cornea is irradiated by using a laser.

4. The method according to claim 1, wherein the step of irradiating the portion of the donor cornea with ultraviolet light comprises irradiating the portion of the donor cornea with ultraviolet light having a wavelength between about 370 nanometers and about 380 nanometers.

5. The method according to claim 1, wherein the step of removing a scarred and/or diseased cornea from the eye of the recipient patient comprises removing substantially the entire thickness of the cornea from the eye of the recipient patient.

6. The method according to claim 1, wherein the step of removing a scarred and/or diseased cornea from the eye of the patient comprises initially cutting away or dissecting a scarred and/or diseased portion of the cornea from a remainder of the cornea using a sharp mechanical instrument, a femtosecond laser, or a combination of a sharp mechanical instrument and a femtosecond laser, and then subsequently removing the scarred and/or diseased portion of the cornea from the eye using a pair of micro-forceps.

7. The method according to claim 6, wherein the sharp mechanical instrument is selected from the group consisting of: (i) a surgical micro-knife, (ii) a needle, (iii) a sharp spatula, and (iv) a pair of micro-scissors.

8. A method of corneal transplantation with a cross-linked cornea, said method comprising the steps of:

removing a scarred and/or diseased portion of a cornea from an eye of a patient;

implanting a portion of a donor cornea into the eye of the patient in a location previously occupied by the scarred and/or diseased portion of the cornea;

applying a photosensitizer to the portion of the donor cornea either prior to the step of implanting the portion of the donor cornea into the eye of the patient or after the step of implanting the portion of the donor cornea into the eye of the patient, the photosensitizer facilitating cross-linking of the donor cornea;

irradiating the portion of the donor cornea with ultraviolet light either prior to the step of implanting the portion of the donor cornea into the eye of the patient or after the step of implanting the portion of the donor cornea into the eye of the patient in order to activate cross-linkers in the portion of the donor cornea, and thereby cross-link the portion of the donor cornea so as to increase a mechanical strength of the donor cornea, kill donor keratocytes in the donor cornea, and make the cross-linked donor cornea less antigenic to the eye of the patient; and after cross-linking and implantation of the portion of the donor cornea, securing the portion of the donor cornea to the eye of the patient using a biocompatible and biodegradable adhesive.

9. The method according to claim 8, wherein the step of removing a scarred and/or diseased portion of a cornea from an eye of a patient comprises removing an external portion of the cornea from outside the eye of the patient.

10. The method according to claim 8, wherein the step of removing a scarred and/or diseased portion of a cornea from an eye of a patient comprises removing the scarred and/or diseased portion of the cornea from the eye of the patient by cutting away the scarred and/or diseased portion of the cornea using a laser.

11. The method according to claim 10, wherein the laser comprises a femtosecond laser.

12. The method according to claim 8, wherein the step of removing a scarred and/or diseased portion of a cornea from an eye of a patient comprises removing an internal portion of the cornea from the eye of the patient.

13. The method according to claim 12, wherein the internal portion of the cornea is removed using forceps.

14. The method according to claim 8, further comprising the step of:

after implantation and cross-linking of the portion of the donor cornea, ablating a portion of the cornea of the patient so as to change the refractive properties of the eye.

15. The method according to claim 14, wherein the portion of the cornea of the patient is ablated using an excimer laser.

16. The method according to claim 8, further comprising the step of:

prior to implantation of the portion of the donor cornea, ablating an external surface or an internal surface of the portion of the donor cornea so as to change the refractive properties of the portion of the donor cornea.

17. The method according to claim 16, wherein the external surface or the internal surface of the portion of the donor cornea is ablated using an excimer laser.

18. The method according to claim 8, further comprising the step of:

prior to implantation of the portion of the donor cornea, ablating an external surface or an internal surface of the cornea of the eye of the patient.

19. The method according to claim 18, wherein the external surface or the internal surface of the cornea of the eye of the patient is ablated using an excimer laser.

20. The method according to claim 8, wherein the biocompatible and biodegradable adhesive that is used to secure the portion of the donor cornea to the eye of the patient does not require externally applied thermal energy for adhesion to the eye of the patient, the biocompatible and biodegradable adhesive including polyethylene glycol mixed with substances selected from the group consisting of gallic acid, gallic tannic acid, chitosan, gelatin, polyphenyl compound, poly(N-isopropylacrylamide), poly(N-vinylpyrrolidone), and combinations thereof.

21. The method according to claim 1, wherein the biocompatible and biodegradable adhesive that is used to secure the cross-linked donor cornea to the eye of the patient does not require externally applied thermal energy for adhesion to the eye of the patient, the biocompatible and biodegradable adhesive including polyethylene glycol mixed with substances selected from the group consisting of gallic acid, gallic tannic acid, chitosan, gelatin, polyphenyl compound, poly(N-isopropylacrylamide), poly(N-vinylpyrrolidone), and a combinations thereof.

22. The method according to claim 8, further comprising the step of:
   injecting mesenchymal stem cells inside the portion of the donor cornea either prior to the step of implanting the portion of the donor cornea into the eye of the patient or after the step of implanting the portion of the donor cornea into the eye.

* * * * *